United States Patent
Büchner et al.

(10) Patent No.: US 8,604,237 B2
(45) Date of Patent: Dec. 10, 2013

(54) METHODS FOR THE PRODUCTION OF L-CARNITINE

(75) Inventors: Thomas Büchner, Naters (CH); Gesa Paradies, Brig (CH)

(73) Assignee: Lonza Ltd, Basel (CH)

( * ) Notice: Subject to any disclaimer, the term of this patent is extended or adjusted under 35 U.S.C. 154(b) by 9 days.

(21) Appl. No.: 12/946,499

(22) Filed: Nov. 15, 2010

(65) Prior Publication Data

US 2011/0118503 A1    May 19, 2011

Related U.S. Application Data

(60) Provisional application No. 61/262,367, filed on Nov. 18, 2009.

(51) Int. Cl.
  *C07B 57/00*    (2006.01)
  *C07C 227/42*   (2006.01)

(52) U.S. Cl.
  USPC ............ 562/401; 562/402; 562/554; 562/557

(58) Field of Classification Search
  CPC .................................................... C07C 227/42
  See application file for complete search history.

(56) References Cited

FOREIGN PATENT DOCUMENTS

| DE | 93347 | | 10/1972 |
|---|---|---|---|
| DE | 3536093 | A1 | 4/1986 |
| DE | 296702 | A5 | 12/1991 |
| DE | 68901889 | T2 | 12/1992 |
| EP | 0195944 | B1 | 10/1991 |
| JP | 2009-102258 | A * | 5/2009 |
| WO | WO2006-028068 | A1 * | 3/2006 |

OTHER PUBLICATIONS

Lorenz et al, Chirality, Application of Preferential Crystallization to Resolve Racemic Compounds in a Hybrid Process, 2006, 18, pp. 828-840.*

Ulrich, Kirk Othmer Encyclopedia of Chemical Technology, 2002, Crystallization, vol. 8, pp. 95-147, obtained online.*

* cited by examiner

*Primary Examiner* — Paul A Zucker

(74) *Attorney, Agent, or Firm* — Hoffmann & Baron, LLP

(57) ABSTRACT

Subject of the invention is a method for the production of L-carnitine, comprising the steps of (a) providing a solution comprising at least 5% (w/w) carnitine in a first solvent, wherein the carnitine is a mixture of D- and L-carnitine,
(b) optionally seeding the solution with L-carnitine crystals,
(c) adding an second solvent, in which the L-carnitine is not soluble or has a low solubility,
(d) isolating crystals comprising L-carnitine.

13 Claims, No Drawings

METHODS FOR THE PRODUCTION OF L-CARNITINE

CROSS-REFERENCE TO RELATED APPLICATION

This application claims the benefit of priority from U.S. Provisional Patent Application No. 61/262,367 filed Nov. 18, 2009, the disclosure of which is incorporated herein by reference.

The invention relates to methods for the production of L-carnitine.

BACKGROUND OF THE INVENTION

Carnitine (vitamin Bt; 3-hydroxy-4-trimethylammoniobutanoate) is a quaternary ammonium compound biosynthesized from the amino acids lysine and methionine. In living cells, it is required for the transport of fatty acids from the cytosol into the mitochondria during the breakdown of lipids for the generation of metabolic energy. It is used as a nutritional supplement.

Carnitine exists in two stereoisomers. The biologically active form is L-carnitine, whilst its enantiomer, D-carnitine, is biologically inactive. When producing L-carnitine in an industrial process, it is desirable to produce the biologically active L-form in high purity. Highly pure L-carnitine can be obtained by microbiological processes. EP 0195944 discloses a microbiological process, in which L-carnitine is produced from crotonobetain and butyrobetain in a bioreactor with the aid of specific microorganisms. A mixture of enantiomeric pure L-carnitine with butyrobetain is obtained. In order to remove the butyrobetain, the final product is recrystallized with methanol and isobutanol.

Another microbiological process for obtaining essentially pure L-carnitine is disclosed by DD 296702. The culturing solution is depleted of L-carnitine by electrodialysis and recrystallization of the L-carnitine. In such microbiological processes, essentially no D-carnitine is produced and thus an enantiomeric separation step is not necessary. A recrystallization of L-carnitine from solvents is applied for removing other substances.

Obtaining highly pure L-carnitine is more complicated when using a non-microbiological or non-enzymatic process. By means of organic synthesis, usually a mixture of D- and L-carnitine is obtained. In order to obtain pure L-carnitine, DE 689 01 889 T2 suggests to apply a ruthenium phosphine complex in a stereoselective asymmetric hydrogenization. Such complexes are relatively complicated and expensive and thus not applicable for the preparation of large amounts of L-carnitine in an industrial process.

Thus methods have been developed for isolating L-carnitine from a mixture of L- and D-carnitine. In general, the methods are based on the conversion of carnitine into a salt with an optically active acid and separation of L- and D-carnitine due to different physical properties, such as solubility.

In this respect, DD 93 347 discloses a method for separating D- and L-carnitine in the presence of camphoric acid, dibenzoyl tartric acid or combinations thereof from alcoholic solutions. The D-carnitine is separated from the L-carnitine due to the different solubility of the salts.

DE 35 36 093 discloses a method for the preparation of L-carnitine from a racemic mixture, in which the D- and L-carnitine are converted to optically active salts with dibenzoyl-L-tartric acid followed by a fractionated crystallization.

However, methods in which the carnitine is converted into an optically active salt or acid are relatively complicated, because they comprise the steps of adding a separating agent and removing it after the separation process. This renders the overall process relatively time- and labour-efficient.

PROBLEM UNDERLYING THE INVENTION

The problem underlying the invention is to provide a process for the production of L-carnitine, which overcomes the above-mentioned problems.

The process should be applicable for producing highly pure L-carnitine from an enantiomeric mixture comprising L- and D-carnitine. The enantiomeric purity shall be increased significantly thereby and the yield shall be high.

The method shall be carried out in a simple manner. Specifically, the use of additional compounds, such as optically active auxiliary agents, which have to be removed afterwards, shall be avoided. Further, the number of process steps shall be relatively low and the process shall not require complicated apparatuses. Overall, the process shall be cost- and labour-efficient.

DISCLOSURE OF THE INVENTION

Surprisingly, the problem underlying the invention is solved by the method according to the claims. Further inventive embodiments are disclosed throughout the description. Subject of the invention is a method for the production of L-carnitine, comprising the steps of
    (a) providing a solution comprising at least 5% (w/w) carnitine in a first solvent, wherein the carnitine is a mixture of D- and L-carnitine,
    (b) optionally seeding the solution with L-carnitine crystals,
    (c) adding a second solvent, in which the L-carnitine is not soluble or has a low solubility, and
    (d) isolating crystals comprising L-carnitine.

Carnitine is a zwitterion, which comprises a carboxy group and a quaternary ammonium group. The carnitine used in step (a) is preferably this zwitterionic carnitine. However, it is also possible to use a salt, such as a chloride, sulphate or nitrate salt. The carnitine used in step (a) is preferably not a salt of a carnitine with an optically active anion.

By the method of the invention, L-carnitine is obtained at enhanced purity. The method of the invention is thus also a method for purifying L-carnitine, or a method for obtaining a highly pure L-carnitine, or a method for increasing the enantiomeric excess of L-carnitine.

According to the invention, crystalline L-carnitine is obtained from a solution comprising D- and L-carnitine. In a preferred embodiment, the solution in step (a) essentially consists of the solvent and carnitine. In the method of the invention, the enantiomeric excess (e.e.) of L-carnitine is enhanced. Preferably, the enantiomeric excess is enhanced by more than 1% or more than 2%. The increase of the enantiomeric excess depends on the enantiomeric excess in the initial solution in step (a). The enantiomeric excess (e.e.) is defined as the absolute difference between the mole fractions of each enantiomer in percent. As an example, a sample with 90% of L-isomer and 10% of D-isomer has an enantiomeric excess of 80% L-isomer.

In preferred embodiments of the invention, in step (a) the carnitine comprises more than 50%, 80%, 90%, 95% or 98% (e.e.) L-carnitine. Preferably, the L-carnitine isolated in step (d) comprises more than 90%, 98%, 99% or 99.5% (e.e.) L-carnitine. Preferably, when a solution in step (a) comprising more than 95% (e.e.) L-carnitine is used, in step (d) crystals comprising more than 99% (e.e.) L-carnitine are obtained.

In a preferred embodiment of the invention, the first solvent is selected from the group consisting of ethanol, methanol, water, acetonitrile and mixtures thereof. The solvent is a good solvent for carnitine. This means that the solubility of carnitine at room temperature is at least 5%, preferably at least 10% or at least 20% (w/w). Preferably, the first solvent is ethanol. In specific embodiments, the first solvent may comprise up to 0.5%, up to 2% or up to 5% (w/w) water. Therefore, the solvent may be technical grade.

In a preferred embodiment, the solution in step (a) is a saturated solution or an oversaturated solution. It is also preferred that the solution is close to saturation, which means that the carnitine concentration is more than 80% or above 90% of the saturation concentration. In a preferred embodiment of the invention, the concentration of total carnitine in the first solvent is 5 to 75%. In ethanol, the concentration is preferably 10 to 50% or 15 to 40% (w/w). In methanol, the concentration is preferably 20 to 70% (w/w).

Preferably, the carnitine dissolved in the solution in step (a) is pure or highly pure carnitine. In this embodiment, the solution in step (a) only comprises minor amounts of additional substances. Based on the amount of total carnitine (D- and L-) in the solution, the amount of additional substances may be below 0.5, below 1 or below 2% (w/w). In another embodiment, the carnitine dissolved in the solution in step (a) comprises a certain amount of side products or other compounds, such as starting compounds from the production process. In this embodiment, the solution in step (a) may comprise up to 5%, up to 10% or up to 15% (w/w) of other compounds, based on the total amount of carnitine. For example, a synthetic carnitine may comprise less than 1% (w/w) hydroxycrotonic acid.

In a preferred embodiment, the solution in step (a) is essentially free of water. This means that the carnitine and the solvent should be essentially free of water or comprise as little water as possible. It was found that the method is more efficient when only a low amount of water is present. Preferably, the overall water content in the solution (a) is below 2%, below 1% or below 0.5% (w/w).

In a preferred embodiment of the invention, step (a) comprises heating the solution, preferably until all the carnitine is dissolved, for example to a temperature above 40° C. or above 50° C. Optionally, residual solid carnitine and/or residual solids can be removed subsequently, for example by filtration. In step (a), the temperature may be adjusted to 40 to 80° C. or 50 to 75° C. The temperature is selected depending on the solvent. When ethanol is used, a temperature between 50 and 75° C. is preferred, for example around 65° C.

In step (b), the solution from step (a) can be seeded with L-carnitine crystals. Preferably, the solution which is seeded is a saturated or oversaturated solution. An oversaturated solution is obtainable when preparing in step (a) a saturated solution at elevated temperature and cooling the saturated solution slowly such that no precipitation or crystallization of carnitine occurs.

By seeding the solution with L-carnitine crystals and incubation, growth of the crystals is induced. Thus, when a seeding step (b) is comprised in the inventive process, the average size of the crystals finally obtained is higher. However, carnitine crystals having a high purity at a high yield can also be obtained without adding seeding crystals in a seeding step (b). The crystals essentially consist of L-carnitine or are enriched in L-carnitine. Only low amounts of seeding crystals are necessary for seeding. The seeding crystals should be highly pure and very fine. The seeding crystals should preferably be added when the solution is still clear, i.e., when no or essentially no crystals or precipitates have formed spontaneously yet. This can be achieved by seeding at enhanced temperature. In a preferred embodiment of the invention, in the seeding step (b) the solution has a temperature of 25 to 50° C., preferably between 30 and 45° C. However, during and after seeding and before adding the second solvent, the solubility of the carnitine is still comparably high, and essentially no or only limited rapid formation of crystals is observed.

In a preferred embodiment, the temperature of the solution is reduced after seeding with the crystals. Preferably, the temperature is reduced to 10 to 30° C., for example to about 20° C.

In a step (c), a second solvent is added, in which the L-carnitine is not soluble or has a low solubility. During and after addition of the second solvent, crystallization of the L-carnitine is observed. During the crystallization of L-carnitine, the solution is depleted of the L-carnitine and becomes a suspension. Thus, after crystallization the composition can be regarded either as a solution or a suspension. When referring to a "solution" with respect to step (b) and consecutive steps, this solution/suspension is meant.

In a preferred embodiment of the invention, the second solvent is selected from acetone, isopropanol, isobutanol, 2-propanol, 1-pentanol, 2-butanone, methylacetate, ethylacetate, butylacetate, tetrahydrofuran, toluene and mixtures thereof. Preferably, the second solvent is acetone.

The second solvent is a solvent, in which L-carnitine is not soluble or only has a low solubility. In a preferred embodiment of the invention, the solubility of L-carnitine in the second solvent is below 3%, below 2% or below 1% (w/w) at 25° C. When adding the second solvent, the overall solubility of carnitine in the solution is decreased, and carnitine is crystallized. Thus upon addition of the second solvent, solid carnitine crystals are formed in the solution.

In a highly preferred embodiment of the invention, the first solvent is ethanol and the second solvent is acetone.

In a preferred embodiment of the invention, in step (c) the ratio of the first solvent to the second solvent is between 1:1 and 1:10 (w/w), more preferably between 1:1.5 and 1:6 or between 1:2 and 1:4 (w/w). The ratio should be adjusted such that the solubility of the carnitine in the solvent mixture is significantly decreased, such that a high portion of the total carnitine is crystallized.

In a preferred embodiment of the invention, after the optional seeding step (b), or before or during step (c), or after adding the second solvent in step (c), the temperature of the solution is adjusting to between 10° C. and 30° C. However, the second solvent can be added before or after reducing the temperature of the solution.

Preferably, the second solvent in step (c) is added slowly, for instance drop wise. In a preferred embodiment of the invention, in step (c) the second solvent is added to the solution for 20 min to 8 h, or for 1 h to 6 h. During the addition of the acetone and incubation, L-carnitine is crystallized. The amount of L-carnitine crystallized usually can be increased by incubation at low temperature.

Preferably, after the addition of the second solvent the composition is incubated at a reduced temperature. For example, the temperature may be reduced to 5 to 20° C., or below 15° C. The composition may be incubated at this temperature for 10 min to 2 days, or for 30 minutes to 24 hours. In a preferred embodiment of the invention, after the addition of the second solvent in step (c) the composition is incubated for 10 min to 2 days at a temperature below 20° C.

In step (d), the solid crystals are isolated by known means, for instance by filtration or sedimentation. Optionally, the crystals are washed, preferably with the second solvent. The solvent is removed by drying, optionally at reduced pressure. Fort instance, acetone may be removed by drying at 55° C. at a pressure below 100 mbar.

According to the invention, the total solid carnitine isolated in step (d) is referred to as "crystals". The solid was found to have a crystalline structure. However, especially upon rapid addition of the second solvent, the solid carnitine "crystals" might also comprise, at least in part, a carnitine precipitate.

The overall yield of L-carnitine, based on the total L-carnitine in the starting solution, is preferably above 80% or above 85%.

In a preferred embodiment of the invention, the method comprises the steps of
(a) providing a solution comprising at least 5% (w/w) carnitine in ethanol, wherein the carnitine comprises at least 50% (e.e.) L-carnitine, wherein the solution is heated until all the carnitine is dissolved,
(a1) adjusting the temperature of the solution to 25 to 50° C.,
(b) seeding the solution with L-carnitine crystals
(b1) optionally adjusting the temperature to 10 to 30° C.,
(c) adding acetone in an amount such that the ratio ethanol/acetone is between 1:1 and 1:10 (w/w),
(c1) optionally cooling the composition to a temperature below 20° C., and
(d) isolating crystals comprising L-carnitine, preferably by filtration.

In the method recited above, steps (a) to (d) are carried out consecutively.

In a specific embodiment of the invention, the overall method of the invention is repeated with the crystals obtained in step (d). In this embodiment, a solution of crystals in a first solvent is prepared. When repeating the overall process twice or more, a highly pure L-carnitine is obtainable even from a carnitine of low enantiomeric purity.

The inventive process solves the above-mentioned problem. A highly pure L-carnitine is obtainable from a mixture of D- and L-carnitine by the inventive process. When separating the mixture of D- and L-carnitine, it is not necessary to add optically active compounds, as for example disclosed in DE 35 36 093 or DD 93 347. In the inventive process, the carnitine is not converted to an optically active salt in an intermediate step. It was surprising that the inventive process is highly efficient, because it was generally assumed in the art that an effective separation of a zwitterion is difficult without optically active additives (see DD 93 347, column 2, lines 8-11). It thus could not be assumed that by the relatively simple process of the invention a high increase of the L-enantiomeric form would be obtained.

The inventive method is applicable in a simple manner with a low number of process steps. The process does not require the precipitation of optically active salts of L-carnitine, isolation and decomposition by additional crystallization steps. The process provides L-carnitine at high enantiomeric purity and also at high yield. The process is less cost- and labour-intensive, compared to processes known in the art. It can be used to purify L-carnitine from enantiomeric mixtures, for instance those obtained by industrial synthesis processes.

EXAMPLES

Example 1

A laboratory reactor is charged with 100 g of carnitine and 300 g of ethanol. The reactor is heated up to 65° C. and stirred until all carnitine has been dissolved. Afterwards the reactor temperature is set to 37° C. At 37° C. seed crystals of pure L-carnitine are added. The reactor temperature is cooled down to 20° C. at a rate of −0.2K/min. At 20° C. 900 g of acetone are added within 2 hours. Afterwards the suspension is cooled down to 10° C. At 10° C. the solids are isolated and washed with acetone and dried at 55° C. and <100 mbar.

As a result, 86.1 g of a crystalline-white dry solid were obtained. The solid comprised 99.036% (w/w) of total carnitine. The enantiomeric purity was 99.60% (e.e.). The residual solvent content was 349 mg/kg ethanol and 386 mg/kg acetone. The total yield of L-carnitine was 88.6%.

Example 2

A laboratory reactor is charged with 60.2 g of carnitine and 60 g of methanol. The reactor is heated up to 50° C. and stirred until all carnitine has been dissolved. Afterwards the reactor temperature is set to 25° C. At 25° C. 0.74 g of seed crystals of pure L-carnitine are added. The reactor temperature is cooled down to 20° C. at a rate of −0.2K/min. At 20° C. 180 g of acetone are added within 1 hour. Afterwards the suspension is cooled down to 10° C. within 50 min. The suspension is stirred at this temperature for another 30 min. Afterwards the solids are filtered via a Nutsch filter and washed twice with approximately 60 g of acetone and subsequently dried for 8 h at 55° C. and a pressure of 250 mbar.

As a result, 45.78 g of a crystalline-white dry solid were obtained. The solid comprised 98.94% (w/w) of total carnitine. The enantiomeric purity was 99.78% (e.e.).

Example 3

A laboratory reactor is charged with 30.1 g of carnitine and 90 g of ethanol. The reactor is heated up to 65° C. and stirred until all carnitine has been dissolved. Afterwards the reactor temperature is set to 37° C. At 37° C. 0.91 g of seed crystals of pure L-carnitine are added. The reactor temperature is cooled down to 20° C. at a rate of −0.2K/min. At 20° C. 270 g of ethyl acetate are added within 1 hour. Afterwards the suspension is cooled down to 10° C. within 50 min. The suspension is stirred at this temperature for another 30 min. Afterwards the solids are filtered via a Nutsch filter and washed twice with approximately 30 g of ethyl acetate and subsequently dried for 8 h at 55° C. and a pressure of 250 mbar.

As a result, 28.66 g of a crystalline-white dry solid were obtained. The solid comprised 98.51% (w/w) of total carnitine. The enantiomeric purity was 99.46% (e.e.).

The invention claimed is:

1. A method for the production of L-carnitine, comprising the steps of
(a) providing a solution comprising at least 5% (w/w) carnitine in a first solvent, wherein the carnitine is a mixture of a mole fraction of D-carnitine and a mole fraction of L-carnitine, wherein the L-carnitine has an enantiomeric excess with respect to the D-carnitine, and wherein the enantiomeric excess is defined as the absolute difference between the mole fraction of L-carnitine and the mole fraction of D-carnitine in percent,
(b) optionally seeding the solution with L-carnitine crystals,
(c) adding a second solvent, in which the L-carnitine is not soluble or has a low solubility, and
(d) isolating crystals comprising L-carnitine,
wherein the first solvent is selected from the group consisting of ethanol, methanol, water, acetonitrile and mixtures thereof, and wherein the second solvent is selected from acetone, 2-butanone, methylacetate, ethylacetate, butylacetate, tetrahydrofuran, toluene and mixtures thereof,
wherein in steps (a) to (d) the enantiomeric excess of the L-carnitine is enhanced by more than 2%.

2. The method of claim 1, wherein in step (a) the concentration of total carnitine in the first solvent is 5 to 75% (w/w).

3. The method of claim 1, wherein in step (a) the carnitine comprises more than 80% (e.e.) L-carnitine and in step (d) the crystals comprise more than 95% (e.e.) L-carnitine.

4. The method of claim 1, wherein step (a) comprises heating the solution to a temperature of above 40° C.

5. The method of claim 1, wherein the solubility of L-carnitine in the second solvent is below 2% (w/w) at 25° C.

6. The method of claim 1, wherein in the seeding step (b) the solution has a temperature of 25 to 50° C.

7. The method of claim 1, wherein in step (c) the ratio of the first solvent to the second solvent is between 1:1 and 1:10 (w/w).

8. The method of claim 1, wherein after the seeding step (b), before or during step (c), or after adding the second solvent in step (c), the temperature of the solution is adjusted to between 10° C. and 30° C.

9. The method of claim 1, wherein in step (c) the second solvent is added to the solution during a time span of 20 min to 24 h.

10. The method of claim 1, wherein after the addition of the second solvent in step (c) the composition is incubated for 10 min to 2 days at a temperature below 20° C.

11. The method of claim 1, wherein in step (d) the crystals comprise more than 99% (e.e.) L-carnitine.

12. The method of claim 1, wherein in step (d) the crystals are isolated by filtration or sedimentation.

13. The method of claim 1, wherein the first solvent is ethanol and the second solvent is acetone.

\* \* \* \* \*